(12) United States Patent
Dosta

(10) Patent No.: US 11,266,682 B2
(45) Date of Patent: Mar. 8, 2022

(54) METHOD OF LOCAL EXPOSURE TO BIOLOGICAL TISSUES, TISSUE-SUBSTITUTE APPLICATOR AND USE OF POROUS POLYTETRAFLUOROETHYLENE

(71) Applicant: Anatoli D. Dosta, Minsk (BY)

(72) Inventor: Anatoli D. Dosta, Minsk (BY)

( * ) Notice: Subject to any disclaimer, the term of this patent is extended or adjusted under 35 U.S.C. 154(b) by 35 days.

(21) Appl. No.: 16/887,100

(22) Filed: May 29, 2020

(65) Prior Publication Data
US 2020/0289549 A1 Sep. 17, 2020

Related U.S. Application Data

(63) Continuation of application No. PCT/BY2017/000018, filed on Nov. 30, 2017.

(51) Int. Cl.
*A01N 35/06* (2006.01)
*A61K 31/755* (2006.01)
*A61L 31/04* (2006.01)

(52) U.S. Cl.
CPC .......... *A61K 31/755* (2013.01); *A61L 31/048* (2013.01)

(58) Field of Classification Search
None
See application file for complete search history.

(56) References Cited

U.S. PATENT DOCUMENTS 4,791,930 A * 12/1988 Suzuki .................. A61F 7/10
607/96

6,997,863 B2 2/2006 Handy et al.
(Continued)

FOREIGN PATENT DOCUMENTS

BY 10325 C1 2/2008
EP 0194446 A1 9/1986
RU 2497489 C1 11/2013
(Continued)

OTHER PUBLICATIONS

International Search Report from PCT/BY2017/000018, filed Nov. 30, 2017, dated Aug. 10, 2018.
(Continued)

*Primary Examiner* — Dominic Lazaro
(74) *Attorney, Agent, or Firm* — Patentbar International PC

(57) ABSTRACT

The invention concerns medical applications and can be used in oncology, as well as in neurosurgery, traumatology, neurology, rehabilitation. The aim of the inventions claimed is the creation of a new method of local exposure on biological tissues and a new tissue-substitute applicator that benefits to both destruction and replacement of tumor tissue by restored biological tissue with no external exposure applied (alternating magnetic field, heating, etc.) The aim set is solved by using porous polytetrafluoroethylene as a cytostatic material. The aim set is also achieved by using porous polytetrafluoroethylene in production of a tissue-substitute applicator for treating or replacing tumor tissues. The aim set for the method of local exposure to biological tissues, including the placement of a tissue-substitute polymeric applicator in direct contact with the biological tissue to be exposed, is solved by using porous polytetrafluoroethylene for the constituent polymeric material.

4 Claims, 6 Drawing Sheets

(56) References Cited

U.S. PATENT DOCUMENTS 8,119,165 B2 2/2012 Peyman
2014/0308336 A1 10/2014 Indolfi et al.

FOREIGN PATENT DOCUMENTS

RU 2506971 C1 2/2014
WO 2017/120608 A1 7/2017

OTHER PUBLICATIONS

Shinkai, M., et al., Intracellular Hyperthermia for Cancer Using Magnetite Cationic Liposomes: In vitro Study, Jpn. J. Cancer Res., Nov. 1996, pp. 1179-1183, vol. 87.
Yanase, M., et al., Antitumor Immunity Induction by Intracellular Hyperthermia Using Magnetite Cationic Liposomes, Jpn. J. Cancer Res., Jul. 1998, pp. 775-782, vol. 89.
Matsuno H., et al., Interstitial Hyperthermia Using Magnetite Cationic Liposomes Inhibit to Tumor Growth of VX-7 Transplanted Tumor In Rabbit Tongue, Jpn. J. Hyperthermic Oncol., 2001, pp. 141-149, vol. 17, No. 3.
Suzuki, M., et al., Anticancer Effect and Immune Induction by Hyperthermia of Malignant Melanoma Using Magnetite Cationic Liposomes, Melanoma Research 2003, pp. 129-135, vol. 13. No. 2.
Matsuoka, F. et al., Hyperthermia Using Magnetite Cationic Liposomes for Hamster Osteosarcoma, BioMagnetic Research and Technology, Mar. 25, 2004, v. 2:3.
Heidari, M. et al, Effect of Magnetic Fluid Hyperthermia on Implanted Melanoma in Mouse Models, Iran J Med Sci., Jul. 2016, vol. 41, No. 4, pp. 314-321.
Choi, K.H. et al., Size-Dependent Photodynamic Anticancer Activity of Biocompatible Multifunctional Magnetic Submicron Particles in Prostate Cancer Cells, Molecules, 2016, 21, 1187.
Ito, A., et al., Augmentation of MHC Class I Antigen Presentation Via Heat Shock Protein Expression By Hyperthermia, Cancer Immunology, Immunotherapy, Nov. 7, 2001, pp. 515-522, v. 50.
Chugunov, Anton, Invisible Frontier: Where Nano and Bio Collide, Cosmetics and Medicine Magazine, 2010, No. 1, https://biomolecula.ru/articles/nevidimaia-granitsa-gde-stalkivaiutsia-nano-i-bio.

\* cited by examiner

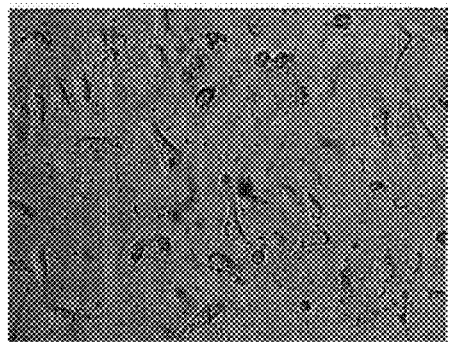
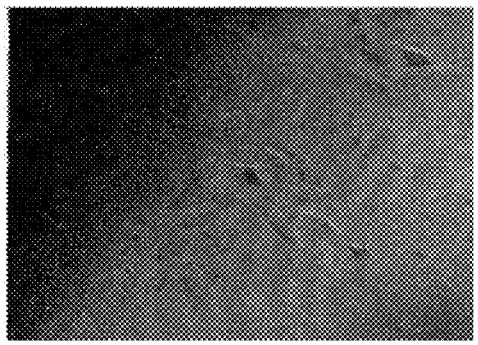
FIG 4A		FIG 4B
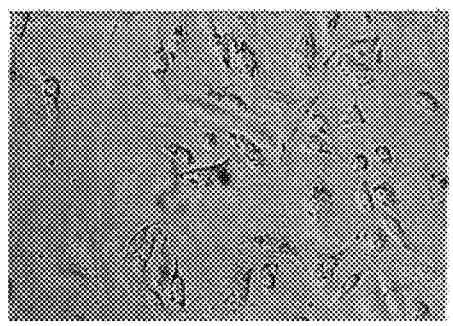
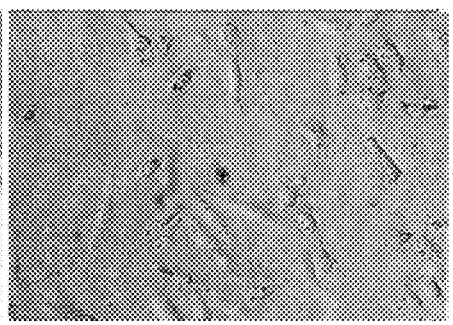
FIG 5A		FIG 5B

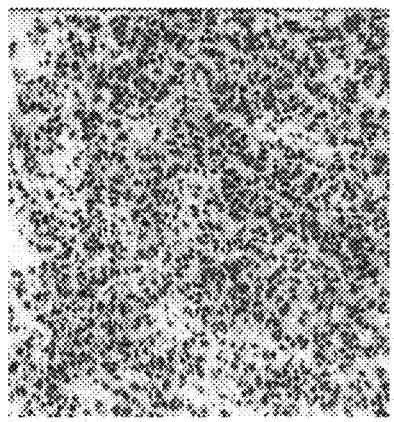 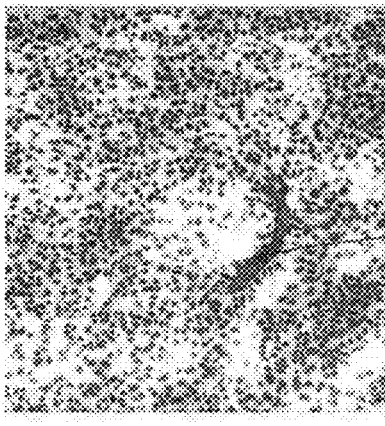 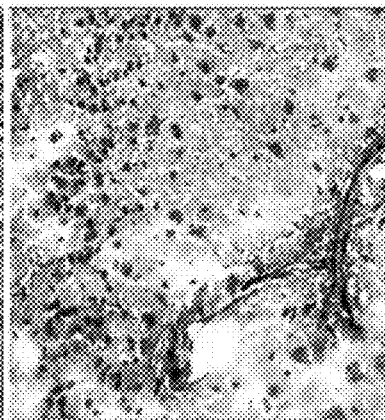
FIG 6A    FIG 6B    FIG 6C
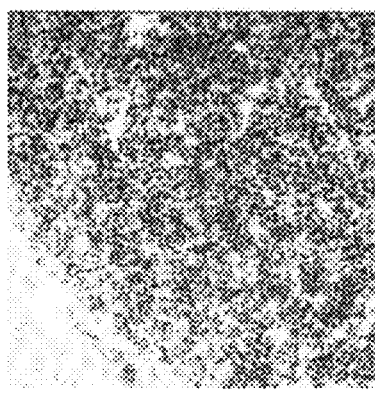 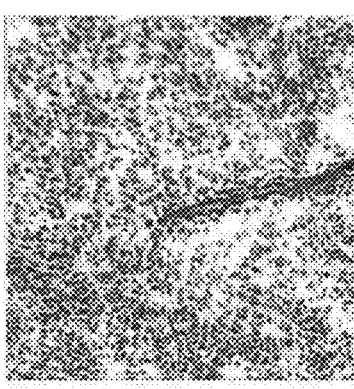 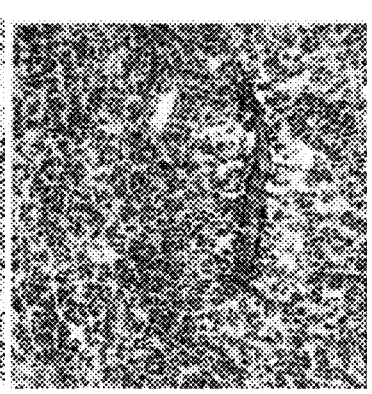
FIG 7A    FIG 7B    FIG 7C

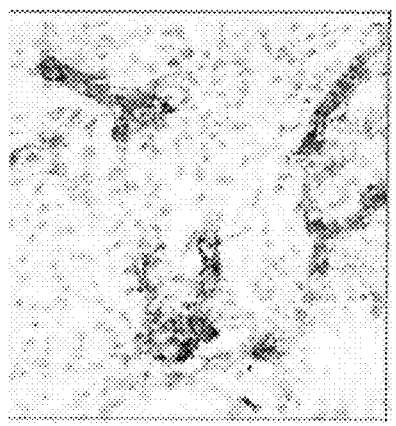 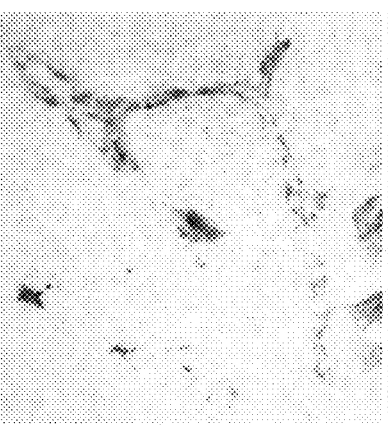 
FIG 8A                    FIG 8B                    FIG 8C

METHOD OF LOCAL EXPOSURE TO BIOLOGICAL TISSUES, TISSUE-SUBSTITUTE APPLICATOR AND USE OF POROUS POLYTETRAFLUOROETHYLENE

RELATED APPLICATIONS

This Application is a Continuation application of International Application PCT/BY2017/000018, filed on Nov. 30, 2017, which is incorporated herein by reference in its entirety.

FIELD OF THE INVENTION

The invention concerns medical applications and can be used in oncology, as well as in neurosurgery, traumatology, neurology, rehabilitation.

BACKGROUND OF THE INVENTION

Methods of treating oncological diseases involving intratumoral injection of nanoparticles are well known. For example, application of liposomes—artificial phospholipid bilayer membranes which surface can be chemically modified to achieve their affinity for the target tissues. Thus, liposomes with positive surface charge have a 10-fold greater affinity for rat glioma cells, as compared to neutrally charged magnetoliposomes [Shinkai M., Yanase M., Honda H., Wakabayashi T., Yoshida J., Kobayashi T. Intracellular hyperthermia for cancer using magnetite cationic liposome: in vitro study. // Jpn. J. Cancer Res. 1996. V. 87. P. 1179-1183]. The hyperthermia technique using magnitocathionic liposomes injected subcutaneously into tumor tissues was proved to be efficient in animals with various types of tumors, such as B-16 melanoma in mice, T-9 glioma in rats, Os 515 osteosarcoma in hamsters, VX-7 squamous carcinoma of rabbit tongue [Yanase M., Shinkai M., Honda H., Wakabayashi T., Yoshida J., Kobayashi, T. Antitumor immunity induction by intracellular hyperthermia using magnetite cationic liposomes. // Jpn. J. Cancer Res. 1998. V. 89. P. 775-782; Matsuno H., Tohnai I., Mitsudo K., Hayashi Y., Ito M., Shinkai M., Kobayashi T., Yoshida J., Ueda M. Interstitial hyperthermia using magnetite cationic liposomes inhibit to tumor growth of VX-7 transplanted tumor in rabbit tongue. // Jpn. J. Hyperthermic Oncol. 2001. V. 17. P. 141-149; Suzuki M., Shinkai M., Honda H., Kobayashi T. Anticancer effect and immune induction by hyperthermia of malignant melanoma using magnetite cationic liposomes. // Melanoma Res. 2003. V. 13. P. 129-135; Matsuoka F., Shinkai M., Honda H., Kubo T., Sugita T., Kobayashi, T. Hyperthermia using magnetite cationic liposomes for hamster osteosarcoma. Biomagn. // Res. Technol. 2004, No 2. P. 3.]. To achieve the complete tumor regression, multiple exposures of animals to alternating magnetic field are essential: this method was successfully tested by Ito et al. for full regression of mammary carcinoma sized 15 mm and more in mice [Ito A., Shinkai M., Honda H., Wakabayashi T., Yoshida J., Kobayashi, T. Augmentation of MHC class I antigen presentation via heat shock protein expression by hyperthermia. // Cancer Immmunol. Immunother. 2001.V. 50. P. 515-522].

Different methods are being developed for introducing particles (preferably nanosized) into tumors, followed by temperature increase locally by external application of magnetic or electromagnetic fields to effect precise hyperthermic destruction of malignant tissues [Russian Patent No. 2506971, Publ. Feb. 20, 2014; U.S. Pat. No. 6,997,863, Publ. Feb. 14, 2006; U.S. Pat. No. 8,119,165, Publ. Feb. 21, 2012]. The research area relates to mesomechanics and energy dissipation in magnetic microparticle systems of various nature (diamagnetic and paramagnetic particles, including living cells and ferroparticles), suspended in simple and rheologically complex fluids and excited by high-intensity and high-gradient magnetic fields (volumetric electromagnetic heating of dielectric materials due to energy absorption in microparticles with magnetic hysteresis, in particular, substantiation of local ferromagnetic hyperthermia of malignant tumors). The application of 9 nm Fe0.5Zn0.5Fe2O4 nanoparticles is not accompanied by an effective temperature increase under the influence of external magnetic field in the mice melanoma model [Heidari M, Sattarahmady N, Javadpour S, Azarpira N, Heli H, Mehdizadeh A, Rajaei A, Zare T. Effect of Magnetic Fluid Hyperthermia on Implanted Melanoma in Mouse Models//Iran J Med Sci. 2016 July; 41(4): 314-321. PMCID: PMC4912650]. Thus, the antitumor effect depends on the size and specific surface area of particles (the number of molecules increases with decreasing their size, while the surface area increases) [Choi K H, Nam K C, Malkinski L, Choi E H, Jung J S, Park B J. Size-Dependent Photodynamic Anticancer Activity of Biocompatible Multifunctional Magnetic Submicron Particles in Prostate Cancer Cells // Molecules. 2016 Sep. 6; 21(9). pii: E1187. doi: 10.3390/molecules21091187].

The nanoparticle biocompatibility depends on the size, ζ-potential in solution, hydrophobicity. Hydrophobic particles have a very short lifetime in bloodstream, since they are rapidly excreted from the body by liver and spleen. Schematically, the particle extraction paths can be represented as follows: particles sized <8 nm are excreted by kidneys; those sized >200 nm—by liver, spleen; ~30 nm—by bile ducts, but accumulating in lungs; particles sized 30 to 200 nm passively accumulate in the tumor sites, under the mechanism: "enhanced permeation and retention" (EPR-effect). This is due to increased blood flow and decreased lymphatic drainage in tumors. In the presence of particles with positive surface charge, cationic particles are toxic in most cases and cause hemolysis and aggregation of erythrocytes [(https://biomolecula.ru/articles/nevidimaia-granitsa-gde-stalkivaiutsia-nano-i-bio)].

Such treatment method is rather ineffective also due to active blood flow in the tumor region, which cause these particles to be quickly removed by blood stream. However, since these nanoparticles remain in the body, removing nanoparticles from the organism in general is a burning problem.

Nanomaterials are proved to feature self-assembly and self-organization properties. The adjustment processes during self-assembly are regulated by competitive effects of various interaction forces of molecular nature, i.e.: hydrophilic-hydrophobic interactions, gravitational forces, van der Waals or Coulomb interactions. In the process of an ordered supermolecular structure or medium formation, only the initial structure components that add to or "collect" the resulting complex structure as its integral parts can participate as an essentially unchanged form. Self-organization can be used as a mechanism for creating complex "templates", processes and structures at a higher hierarchical organization level, as compared to the original source system, due to numerous and multivariate interactions of components at low levels involving local interaction laws, being different from the collective laws of behavior of the resulting architecture. The conformations of nanoparticles in the living body result in numerous functional shifts, with the toxic effect being a dominating factor. It is the toxicity of nanoparticles that limits their wide application in the areas of diagnostics and therapy, incidentally, with periodic suppression of this indisputable fact.

Due to their specific properties, nanoparticles tend to unite and form conglomerates of micrometer sizes in the excretory system (in blood and/or lymphatic vessels).

The nearest Prior Art reference to the method claimed and to the tissue-substitute applicator claimed is Russian Patent No. 2497489, Publ. Nov. 10, 2013, where the method of local exposure to biological tissues incorporates the phase of locating a tissue-substitute applicator, made of polymeric material with addition of electrically conductive ferromagnetic particles sized 200-1000 μm, in direct contact with the biological tissue to be exposed. Next, the induction heating of the tissue-substitute applicator and adjacent biological tissues by alternating HF magnetic field application is performed to create a hyperthermal effect in order to destroy the tumor tissue.

The drawbacks of these technological solutions include, firstly, the effect of possible spread of tumor-inducing agents into adjacent tissues when heating and destroying tumor cells.

In addition, the disintegration of tumor tissues causes increased concentration of toxic substances, which are rather difficult to remove from the body. To minimize the toxic exposure, operators try to minimize the area of the exposure, to calculate the volume of tissue to be destroyed, taking into account the excretory capacity of the lymphatic and circulatory systems, both at the cell level and at the excretory organ level (kidneys and liver). If possible, the destroyed tissues are removed, for example, by washing.

Another disadvantage of the method refers to the complexity of equipment required for its implementation.

SUMMARY OF THE INVENTION

The aim of the inventions claimed is the creation of a new method of local exposure on biological tissues and a new tissue-substitute applicator that benefits to both destruction and replacement of tumor tissue by restored biological tissue with no external exposure applied (alternating magnetic field, heating, etc.)

The aim set for the method of local exposure to biological tissues, including the placement of a tissue-substitute polymeric applicator in direct contact with the biological tissue to be exposed, is solved by using porous polytetrafluoroethylene for the constituent polymeric material.

Within the framework of this method, it is possible to apply exposure both to the tumor biological tissue and to the surrounding biological tissue.

The aim set for the tissue-substitute polymeric applicator to place the same in direct contact with the tumor tissue is solved by applying porous polytetrafluoroethylene for the constituent material.

When studying the resources to inhibit the nanoparticles escape from tumor, the authors chose porous polytetrafluoroethylene ("PTFE") for the constituent polymeric carrier of electrically conductive ferromagnetic nanoparticles, expecting the tumor tissues to germinate into PTFE pores and to hold these particles nearby, thus preventing from their carrying-out by blood flow. However, in the course of these studies, cytostatic properties of porous PTFE were also detected.

Thus, the aim was solved by using porous polytetrafluoroethylene as a cytostatic material.

The aim was also achieved by using porous polytetrafluoroethylene in production of a tissue-substitute applicator for treating or replacing tumor tissues.

BRIEF DESCRIPTION OF THE DRAWINGS

This invention is explained in detail at the following non-restrictive drawings.

FIGS. 4A-4B show the results of in vitro study of the porous PTFE effects on healthy cell culture (fibroblasts, in this case).

FIGS. 5A-5B show the results of in vitro study of the porous PTFE effects on healthy cell culture (fibroblasts, in this case).

FIG. 6A shows a cryostat section of Wistar rat brain tissue at 30 days following C6 glioma xenograft implantation;

FIG. 6B shows a cryostat section of Wistar rat brain tissue at 30 days following the placement of C6 glioma xenograft and porous PTFE tissue-substitute applicator;

FIG. 6C shows a cryostat section of Wistar rat brain tissue at 30 days following the porous PTFE tissue-substitute applicator implantation;

FIG. 7A shows a cryostat section of Wistar rat brain tissue at 30 days following C6 glioma xenograft implantation;

FIG. 7B shows a cryostat section of Wistar rat brain tissue at 30 days following C6 glioma xenograft and porous PTFE tissue-substitute applicator implantation;

FIG. 7C shows a cryostat section of Wistar rat brain tissue at 30 days following porous PTFE, tissue-substitute applicator implantation;

FIG. 8A shows a cryostat section of Wistar rat brain tissue at 30 days following C6 glioma xenograft implantation;

FIG. 8B shows a cryostat section of Wistar rat brain tissue at 30 days following C6 glioma xenograft and porous PTFE tissue-substitute applicator implantation;

FIG. 8C shows a cryostat section of Wistar rat brain tissue at 30 days following porous PTFE tissue-substitute applicator;

DETAILED DESCRIPTION OF THE PREFERRED EMBODIMENTS

Figure 1:
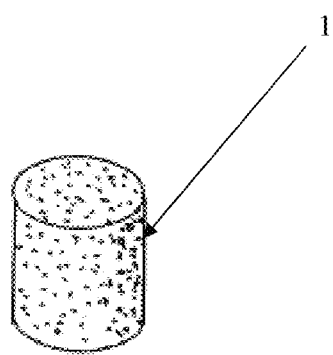
FIG. 1 shows a schematic representation of the claimed tissue-substitute applicator.

The claimed tissue-substitute applicator 1 (see FIG. 1) can be manufactured by the method, as described, for example, in Belarusian Patent No. 10325, Publ. Feb. 28, 2008. The tissue-substitute porous PTFE applicator is made by mixing the source material granules with porophore granules (sodium chloride), compressing the resulting mixture, washing away the sodium chloride residues from the resulting porous pre-form, followed by sintering process. The complex pore structure is attained, in this case, by use of porophore granules of comminuted shape. The dimensions of dead-end pores depend on fine porophore granule sizes, and the dimensions of open pores are determined by the size of the porophore larger fraction granules.

To test the feasibility and effectiveness of the claimed method, tissue-substitute applicator and PTFE performance, animal tests were performed, as shown in the examples below.

Example 1

To determine the porous PTFE cytotoxicity for tumor and healthy cells, two series of in vitro studies were carried out.

First Series:

Tumor cells were introduced into culture medium (in this study, C6 glioma); one medium portion was left intact for reference, the other one placed a porous PTFE tissue-substitute applicator.

Figures 2A, 2B:
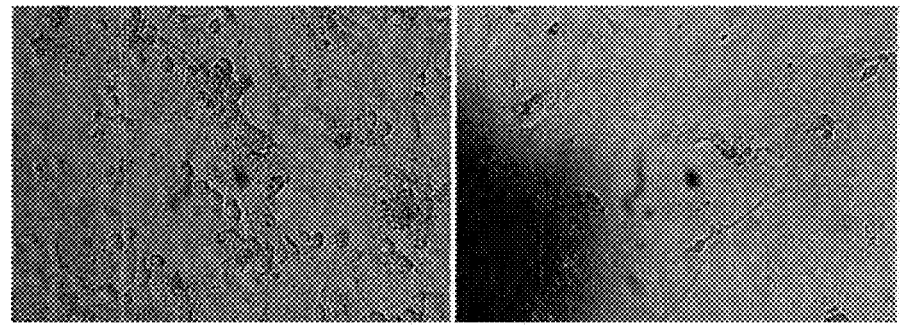
FIGS. 2A-2B show the results of in vitro study of the porous PTFE effect on tumor cell culture (glioma, in this case).
Figures 3A, 3B:
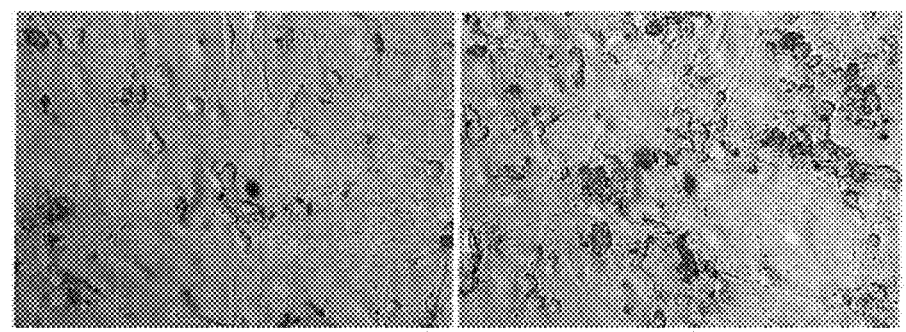
FIGS. 3A-3B show the results of in vitro study of the porous PTFE effect on tumor cell culture (glioma, in this case).

After 48 hours of follow-up, the following pictures were taken:

C6 glioma intact cells distribution (FIG. 2A, 70±3% confluence) and C6 glioma cells distribution following placement of porous PTFE tissue-substitute applicator (FIG. 2B, 20±4% confluence);

C6 glioma intact cells monolayer, trypan blue staining (FIG. 3A, C6 glioma intact cells viability—90±3%), and C6 glioma cells monolayer with porous PTFE tissue-substitute applicator (FIG. 3B, C6 glioma cells viability with porous PTFE tissue-substitute applicator—55±3%)

Thus, during this series of studies, porous PTFE was found to demonstrate in vitro cytotoxicity against C6 glioma cells culture.

Second Series:

Healthy cells were introduced into culture medium (in this study—fibroblasts); one medium portion was left intact for reference, the other one placed a porous PTFE tissue-substitute applicator.

After 48 hours of follow-up, the following pictures were taken:

intact fibroblasts distribution (FIG. 4A, 53±3% confluence) and fibroblasts distribution following placement of porous PTFE tissue-substitute applicator (FIG. 4B, 35±4% confluence);

intact fibroblasts monolayer, trypan blue staining (FIG. 5A, intact fibroblasts viability—99±3%), and fibroblasts monolayer with porous PTFE tissue-substitute applicator (FIG. 5B, fibroblasts viability with porous PTFE tissue-substitute applicator—98±3%).

Thus, during this series of studies, it was reported that porous PTFE did not exhibit in vitro cytotoxicity against healthy cells, in particular fibroblasts.

Example 2

The in vivo study focused on cerebral cortex test of Wistar rats, divided into 3 groups: Group 1—rats with C6 glioma xenografts implanted in sensorimotor cortex for 1 month (30 days); Group 2—rats with C6 glioma xenografts and porous PTFE tissue-substitute applicators implanted in sensorimotor cortex for 1 month (30 days); Group 3—rats with porous PTFE tissue-substitute applicators only implanted in sensorimotor cortex for 1 month (30 days).

The study applied histological (hematoxylin and eosin staining), neurohistological (Nissl staining) and histochemical investigation methods (acetylcholinesterase (AChE) activity detection).

Cryostat sections of Wistar rat brain tissue were stained with hematoxylin and eosin and toluidine blue, followed by light-optical microscopic examination.

FIG. 6A shows a cryostat section of Wistar rat brain tissue at 30 days following C6 glioma xenograft implantation.

C6 glioma consists of small undifferentiated cells with dense polymorphic nuclei. The glial tissue represents vessels inside. Hematoxylin and eosin staining; magnification ×200.

Histological analysis of rat brain transverse sections with experimental C6 glioma at 30 days follow-up revealed the presence of numerous tumor cells with moderate cellular polymorphism. The cells represented an elongated spindle-shaped form, large dark hyperchromic nuclei of irregular shape, thin and slightly colored cytoplasmic layer and short processes. There were multiple mitoses and foci of vacuolization. Inside the cell clusters, vessels of different sizes were detected, as well as newly formed small capillaries.

FIG. 6B shows a cryostat section of Wistar rat brain tissue at 30 days following the placement of C6 glioma xenograft and porous PTFE tissue-substitute applicator.

Porous PTFE tissue-substitute applicator inside tumor tissue. There is a slight reactive swelling of glia around and accumulations of poorly differentiated tumor cells. The tissue-substitute applicator was enclosed in a glial capsule. Hematoxylin and eosin staining; magnification ×200.

Histological analysis of rat brain transverse sections with experimental C6 glioma and tissue-substitute applicator at 30 days post-implantation revealed the formation of a gliomesodermal capsule around the synthetic material, and transparent fields in the adjacent areas, which can be regarded as foci of tumor disintegration, surrounded by clusters of poorly differentiated cells—"pseudopalisades".

FIG. 6C shows a cryostat section of Wistar rat brain tissue at 30 days following the porous PTFE tissue-substitute applicator implantation.

Porous PTFE tissue-substitute applicator implanted in brain gray matter. Hematoxylin and eosin staining; magnification ×200.

The area of the tissue-substitute applicator implantation revealed the formation of a tender scar, consisting of loose gliomeodermal tissue, which fibers germinate into the material pores, and glial capsule surrounding the tissue-substitute applicator. In some areas of the implanted material surface, the capsule walls were thinner due to formation of clear foci in the adjacent cerebral cortex, which could be considered an area of reactive edema. Clusters of fibroblasts and glial cells were also detected there.

Cryostat sections of Wistar rat brain tissue were exposed to Nissl staining, then studied to identify elements of nervous tissue, magnification ×100.

FIG. 7A shows a cryostat section of Wistar rat brain tissue at 30 days following C6 glioma xenograft implantation.

C6 Glioma in Brain Gray Matter

FIG. 7B shows a cryostat section of Wistar rat brain tissue at 30 days following C6 glioma xenograft and porous PTFE tissue-substitute applicator implantation.

Porous PTFE tissue-substitute applicator inside tumor. Moderate reactive swelling of glia that surrounds the tissue-substitute applicator; accumulations of small polymorphous tumor cells.

FIG. 7C shows a cryostat section of Wistar rat brain tissue at 30 days following porous PTFE tissue-substitute applicator implantation.

PTFE synthetic material inside brain gray matter. Activation of glial cells in the tissue-substitute applicator area. Moderate glial reactive swelling around the tissue-substitute applicator.

FIG. 8A shows a cryostat section of Wistar rat brain tissue at 30 days following C6 glioma xenograft implantation.

AChE-positive nerve fibers inside the tumor; magnification ×400.

C6 glioma is represented by small undifferentiated cells with dense polymorphic nuclei. The glial tissue represents vessels inside. This serves an evidence of tumor process activation. Cholinergic nerve fibers, which form loopy conglomerates, follow along the vasculature.

FIG. 8B shows a cryostat section of Wistar rat brain tissue at 30 days following C6 glioma xenograft and porous PTFE tissue-substitute applicator implantation.

AChE-positive nerve fibers in the area of PTFE implantation inside the tumor; magnification ×200. Porous PTFE tissue-substitute applicator trends to develop a moderate reactive edema of glioma cells; a cluster of small polymorphous undifferentiated tumor cells is reported to form a peculiar capsule.

Cholinergic nerve fibers are detected to follow along the vasculature inside the tumor.

FIG. 8C shows a cryostat section of Wistar rat brain tissue at 30 days following porous PTFE tissue-substitute applicator.

AChE-positive nerve fibers in the area of PTFE implantation inside brain gray matter; magnification ×400.

One month following porous PTFE tissue-substitute applicator placement, no necrosis was observed in the implantation area, but reactive edema persisted. The activation of microglial cells, as well as macrophages of the central nervous system migrating from distant brain areas to the tissue-substitute applicator, was reported.

The applicator-surrounding gray matter area represents a network of nerve fibers that follow along the vessels and penetrate into the pores of the tissue-substitute applicator.

Conclusion: After 1 month (30 days) following the implantation of porous PTFE tissue-substitute applicator in rats' cerebral cortex with experimental C6 glioma, foci of tumor disintegration are detected in the adjacent areas surrounding the tissue-substitute applicator. Near the foci, accumulations of poorly differentiated tumor cells are observed, followed by "pseudopalisades" formation. The data obtained may evidence that PTFE material implanted in cerebral cortex benefits to the disintegration of the surrounding tumor tissue.

Example 3

Histological analysis of Wistar rats brain tissue at 4 months' follow-up, following the implantation of porous PTFE tissue-substitute applicators or C6 glioma and porous PTFE tissue-substitute applicators in sensorimotor cortex.

The in vivo study focused on cerebral cortex test of Wistar rats, divided into 2 groups: Group 1—rats with C6 glioma xenografts and porous PTFE tissue-substitute applicators implanted in sensorimotor cortex for 4 months; Group 2—rats with porous PTFE tissue-substitute applicators only implanted in sensorimotor cortex for 4 months.

The study applied histological (hematoxylin and eosin staining), neurohistological (Nissl staining) and histochemical investigation methods (acetylcholinesterase (AChE) activity detection).

Cryostat sections of Wistar rat brain tissue were stained with hematoxylin and eosin and toluidine blue, followed by light-optical microscopic examination. Hemotoxylin-eosin staining for the tissue structure determination involved the use of hematoxylin as the main stain, which stained basophilic cellular structures in bright blue, and alcoholic eosin Y solution, which stained eosinophilic cellular structure in red-pink color. Basophilic structures, as a rule, are those that contain nucleic acids (DNA and RNA): cell nucleus, ribosomes and RNA-rich parts of cytoplasm. Eosinophilic structures contain intra- and extracellular proteins, for example, Lewy bodies. Cytoplasm is an eosinophilic medium. Erythrocytes are always stained in bright red.

Figures 9A, 9B:
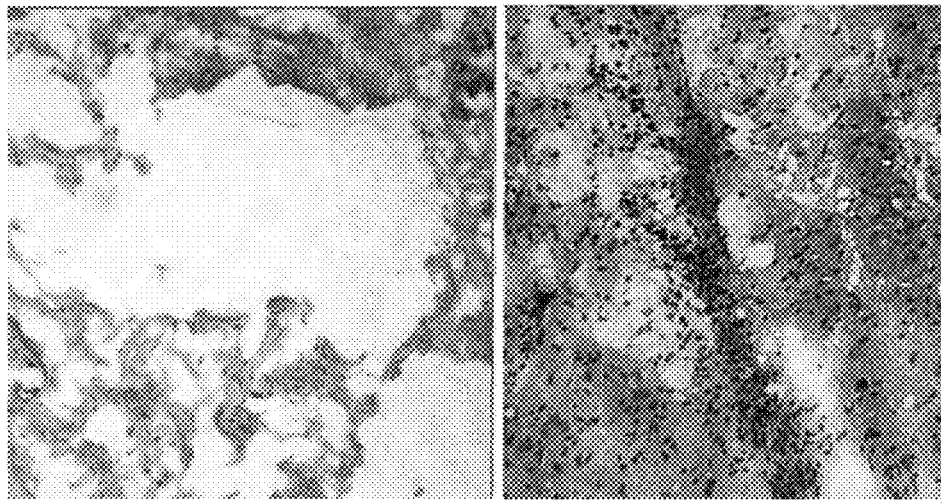
FIG. 9A shows a cryostat section of Wistar rat brain tissue at 4 months following C6 glioma xenograft and porous PTFE tissue-substitute applicator implantation.
FIG. 9B shows a cryostatic section of Wistar rat brain tissue at 4 months following porous PTFE tissue-substitute applicator implantation.

FIG. 9A shows a cryostat section of Wistar rat brain tissue at 4 months following C6 glioma xenograft and porous PTFE tissue-substitute applicator implantation.

Massive foci of tumor tissue disintegration. Stained with hematoxylin and eosin; magnification ×100.

FIG. 9B shows a cryostatic section of Wistar rat brain tissue at 4 months following porous PTFE tissue-substitute applicator implantation.

Porous PTFE tissue-substitute applicator implanted posttrauma in the cerebral cortex of experimental rats (4 months). Substitution of brain defect area with regenerating neural tissue (PTFE—dark brown color) Staining with hematoxylin and eosin; magnification ×100.

Cryostat sections of Wistar rat brain tissue were stained by Nissl method, then studied to identify elements of nervous tissue; magnification ×100.

Figures 10A, 10B:
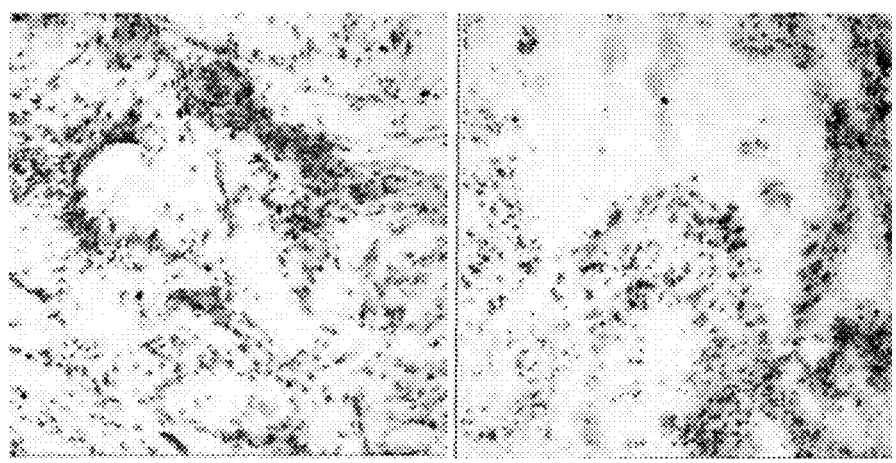
FIG. 10A shows a cryostat section of Wistar rat brain tissue at 4 months following C6 glioma xenograft and porous PTFE tissue-substitute applicator implantation.
FIG. 10B shows a cryostat section of Wistar rat brain tissue at 4 months following porous PTFE tissue-substitute applicator implantation

FIG. 10A shows a cryostat section of Wistar rat brain tissue at 4 months following C6 glioma xenograft and porous PTFE tissue-substitute applicator implantation.

Porous PTFE tissue-substitute applicator implanted in brain tumor tissue of experimental rats (4 months). Microglia cells in the tumor disintegration area. Nissl staining; magnification ×100.

FIG. 10B shows a cryostat section of Wistar rat brain tissue at 4 months following porous PTFE tissue-substitute applicator implantation.

Porous PTFE tissue-substitute applicator implanted posttrauma in the cerebral cortex of experimental rats (4 months). Clusters of microglial cells migrating to the area of damage. Nissl staining, magnification ×100.

Conclusion: After 4 months following the implantation into the tumor cerebral cortex tissue of experimental rats, porous PTFE tissue-substitute applicator benefits to the formation of multiple small foci of colliquated necrosis and massive central foci of tumor tissue disintegration, thus resulting in tumor reduction.

After 4 months following the porous PTFE tissue-substitute applicator implantation into the cerebral cortex damage area in experimental rats, the defect replacement with regenerating neural tissue is observed, accompanied by vascularization and sprouting of cholinergic nerve fibers inside the tissue-substitute applicator.

Histological analysis of rat brain sections with test glioma and porous PTFE tissue-substitute applicator implanted into the tumor tissue revealed numerous small foci of colliquated necrosis of the tumor, as well as massive central foci of tumor tissue decay in the applicator area after 4 months follow-up. Microglia cells migrated to the area of tumor disintegration. In the tumor-remaining areas, polymorphism of cellular structures, numerous multinucleated giant cells with signs of necrobiotic lesion were reported. Tumor areas with completely destroyed parenchyma and partially preserved stroma were revealed.

In the implantation area of porous PTFE tissue-substitute applicator, the tumor tissue revealed single thin cholinergic nerve fibers that follow the newly formed vessels.

Histological analysis of experimental rats brain sections at 4 months post-trauma in the cerebral cortex and following the implantation of porous PTFE tissue-substitute applicator, the development of repair processes in the focus area was demonstrated. On the background of persisting edema of the cerebral cortex, the proliferation of astrocytes in the porous PTFE area was noted, where they accumulated inside the tissue-substitute applicator fibers. There, clusters of microglial cells were also detected which migrated to the damage area and transformed into macrophages. In the cerebral cortex regenerating area adjacent to the porous PTFE tissue-substitute applicator, a vascularization process was observed. The brain defect area was completely replaced by a regenerating neural tissue.

Thin cholinergic nerve fibers were revealed in the brain regeneration area, inside the tissue-substitute applicator, which followed along the vessels between the synthetic PTFE material pores.

FINAL CONCLUSION

After 4 months following the implantation into the tumor cerebral cortex tissue of experimental rats, porous PTFE tissue-substitute applicator benefits to the formation of multiple small foci of colliquated necrosis and massive central foci of tumor tissue disintegration, thus resulting in tumor reduction.

After 4 months following the porous PTFE tissue-substitute applicator implantation into the cerebral cortex damage area in experimental rats, the defect replacement with regenerating neural tissue is observed, accompanied by vascularization and sprouting of cholinergic nerve fibers inside the tissue-substitute applicator.

Based on the results obtained, it can be concluded that the developed technology for manufacturing PTFE-based materials allows the creation of tissue-substitute applicators that are promising for further research for possible biomedical applications.

What is claimed is:

1. A method of local exposure of a biological tissue comprising:
   exposing the biological tissue to porous polytetrafluoroethylene by placing a tissue-substitute polymeric applicator in direct contact with the biological tissue with no external exposure applied to the biological tissue,
   wherein the tissue-substitute polymeric applicator comprises the porous polytetrafluoroethylene as a constituent polymeric material, and
   wherein the biological tissue exposed to the porous polytetrafluoroethylene is a tumor tissue or a tumor-surrounding biological tissue.

2. The method of claim 1, wherein the tissue-substitute polymeric applicator is made of porous polytetrafluoroethylene (PTFE).

3. The method of claim 1, wherein the porous polytetrafluoroethylene is a cytostatic material or a cytotoxic material.

4. A method of using porous polytetrafluoroethylene for local exposure of a biological tissue comprising placing a tissue-substitute porous polytetrafluoroethylene applicator in direct contact with the biological tissue for treating or replacing tumor tissues with no external exposure applied, wherein the porous polytetrafluoroethylene is a cytostatic material or a cytotoxic material.

* * * * *